United States Patent
Olenik et al.

(10) Patent No.: US 8,722,582 B2
(45) Date of Patent: May 13, 2014

(54) THERMODYNAMICALLY STABLE CRYSTAL MODIFICATION OF 2-({2-CHLORO-4-(METHYLSULFONYL)-3-[(2,2,2-TRIFLUOROETHOXY)METHYL]PHENYL}CARBONYL)CYCLOHEXANE-1,3-DIONE

(75) Inventors: Britta Olenik, Bottrop (DE); Andreas Van Almsick, Karben (DE); Marin-Holger Hinz, Hückeswagen (DE); Smita Patel, Eppstein-Bremthal (DE); Frank Sixl, Rechtsupweg (DE); Gerhard Thielking, Burscheid (DE); Sylvia Dworacek, Solingen (DE)

(73) Assignee: Bayer Cropscience AG, Monheim (DE)

( * ) Notice: Subject to any disclaimer, the term of this patent is extended or adjusted under 35 U.S.C. 154(b) by 531 days.

(21) Appl. No.: 12/674,582

(22) Filed: Feb. 22, 2010

(65) Prior Publication Data
US 2011/0212839 A1    Sep. 1, 2011

Related U.S. Application Data

(63) Continuation of application No. PCT/EP2008/006386, filed on Aug. 2, 2008.

(30) Foreign Application Priority Data

Aug. 24, 2007 (EP) .................... 07016606

(51) Int. Cl.
*A01N 35/06* (2006.01)
*A01N 25/12* (2006.01)
(52) U.S. Cl.
CPC ............. *A01N 35/06* (2013.01); *A01N 25/12* (2013.01)
USPC .......................... 504/348; 504/354
(58) Field of Classification Search
CPC ................. A01N 35/06; A01N 25/12
USPC ............................... 504/348, 354
See application file for complete search history.

(56) References Cited

U.S. PATENT DOCUMENTS

| 8,309,769 B2 * | 11/2012 | Hupe et al. | 568/31 |
| 2003/0104946 A1 * | 6/2003 | Bickers et al. | 504/271 |
| 2010/0041557 A1 * | 2/2010 | Hupe et al. | 504/348 |

FOREIGN PATENT DOCUMENTS

| EP | 1314724 A1 | 5/2003 |
| WO | 00/21924 A1 | 4/2000 |
| WO | 03/047340 A2 | 6/2003 |
| WO | 2007/006415 A2 | 1/2007 |

OTHER PUBLICATIONS

Bernstein et al., "Concomitant Polymorphs," Chem. Int. Ed., 1999, 38, 3440-3461.
International Search Report for PCT/EP2008/006386, dated Oct. 27, 2008.
"The Crystal Structure of Acetic Acid," Radiation Laboratory: The Crystal Structure of Acetic Acid, University of California, Berkeley, Contract No. W-7405-eng-48, pp. 2-19, Robert E. Jones, Dec. 14, 1956.
Lange, Norbert A. and Gordon M. Forker, "Handbook of Chemistry: A reference volume for all requiring ready access to chemical and physical data used in laboratory work and manufacturing," Tenth Edition, pp. 304-305 (1961).

\* cited by examiner

*Primary Examiner* — Rebecca Prouty
*Assistant Examiner* — Danielle Sullivan
(74) *Attorney, Agent, or Firm* — Miles & Stockbridge P.C.

(57) ABSTRACT

What is described is a thermodynamically stable crystal modification of the herbicidally active compound 2-({2-chloro-4-(methylsulfonyl)-3-[(2,2,2-trifluoroethoxy)methyl]phenyl}carbonyl)cyclohexan-1,3-dione (tembotrione). This thermodynamically stable crystal modification has particular advantages in the stability of suspension formulations.

11 Claims, 6 Drawing Sheets

THERMODYNAMICALLY STABLE CRYSTAL MODIFICATION OF 2-({2-CHLORO-4-(METHYLSULFONYL)-3-[(2,2,2-TRIFLUOROETHOXY)METHYL]PHENYL}CARBONYL)CYCLOHEXANE-1,3-DIONE

CROSS REFERENCE TO RELATED APPLICATIONS

This application is a Continuation of PCT/EP2008/006386, filed Aug. 2, 2008, which claims priority to European Application No. 07016606.1, filed Aug. 24, 2007.

BACKGROUND OF THE INVENTION

1. Field of the Invention

The invention relates to the technical field of the crop protection agents.

More specifically, it relates to a thermodynamically stable crystal modification of 2-({2-chloro-4-(methy lsulfonyl)-3-[(2,2,2-trifluoroethoxy)methyl]phenyl}carbonyl)cyclohexan-1,3-dione of the formula (hereinbelow referred to as tembotrione), to processes for its preparation and to its use as herbicide.

2. Description of Related Art

It is known that some organic compounds can occur in only one crystal structure while others (so-called polymorphs) can occur in various crystal structures, see, for example, J. Bernstein, R. J. Davey, J. O. Henck, Angew. Chem. Int. Ed., 1999, 38, 3440-3461. Thus, EP 1 314 724 A1 discloses two crystal structures of the herbicidally active compound sulcotrione.

Tembotrione, which is known, for example, from WO 00/21924 (example No. 3 in table 1), has herbicidal properties and is suitable for preparing crop protection compositions used for weed control. However, it has been found that the tembotrione preparable in accordance with the disclosure of WO 00/21924 is not suitable for preparing user-friendly presentation forms. User-friendly presentation forms are, for example, suspension formulations in which tembotrione is present finely ground in solid form. In tests in practice, it has been found that, in suspension formulations, tembotrione preparable in accordance with the disclosure of WO 00/21924 leads to crystal growth and, as a consequence thereof, to agglomeration and precipitation, such that the suspension formulation becomes unusable. The crystal growth may occur spontaneously or over a relatively long period of time and is unpredictable.

SUMMARY OF THE INVENTION

It was an object of the present invention to provide a modification of tembotrione which overcomes these disadvantages and which is suitable for preparing a suspension formulation which is storage-stable for a relatively long period of time.

We have found a thermodynamically stable modification of tembotrione which crystallizes in an orthorhombic system and which does not have the abovementioned disadvantages and is thus suitable for preparing suspension formulations such as suspoconcentrates, suspoemulsiones and oil dispersions.

Accordingly, the invention provides a modification of 2-({2-chloro-4-(methylsulfonyl)-3-[(2,2,2-trifluoroethoxy) methyl]phenyl}carbonyl)cyclohexan-1,3-dione (tembotrione) which crystallizes in an orthorhombic system.

DETAILED DESCRIPTION OF A PREFERRED EMBODIMENT

In the context of the present invention, it was found that tembotrione, in addition to the stable modification crystallizing in an orthorhombic system, also occurs in at least two metastable modifications.

Hereinbelow, the terms "stable modification I", "stable crystal modification I", "thermodynamically stable modification I" and "thermodynamically stable crystal modification I" are to be understood as being equivalent.

Figure 1:
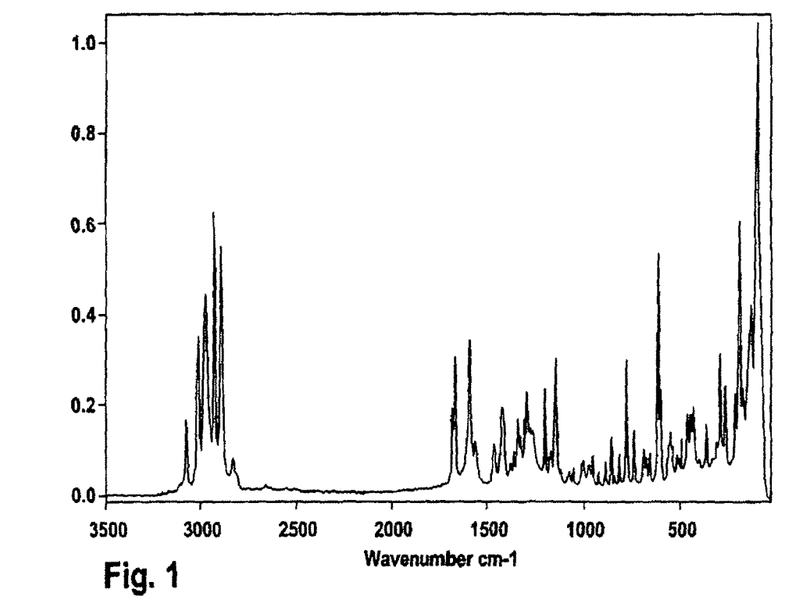
FIG. 1 shows the Raman spectrum of the crystal modification I of tembotrione. The values of the band maxima in wave numbers are listed in table 1.
Figure 1A:
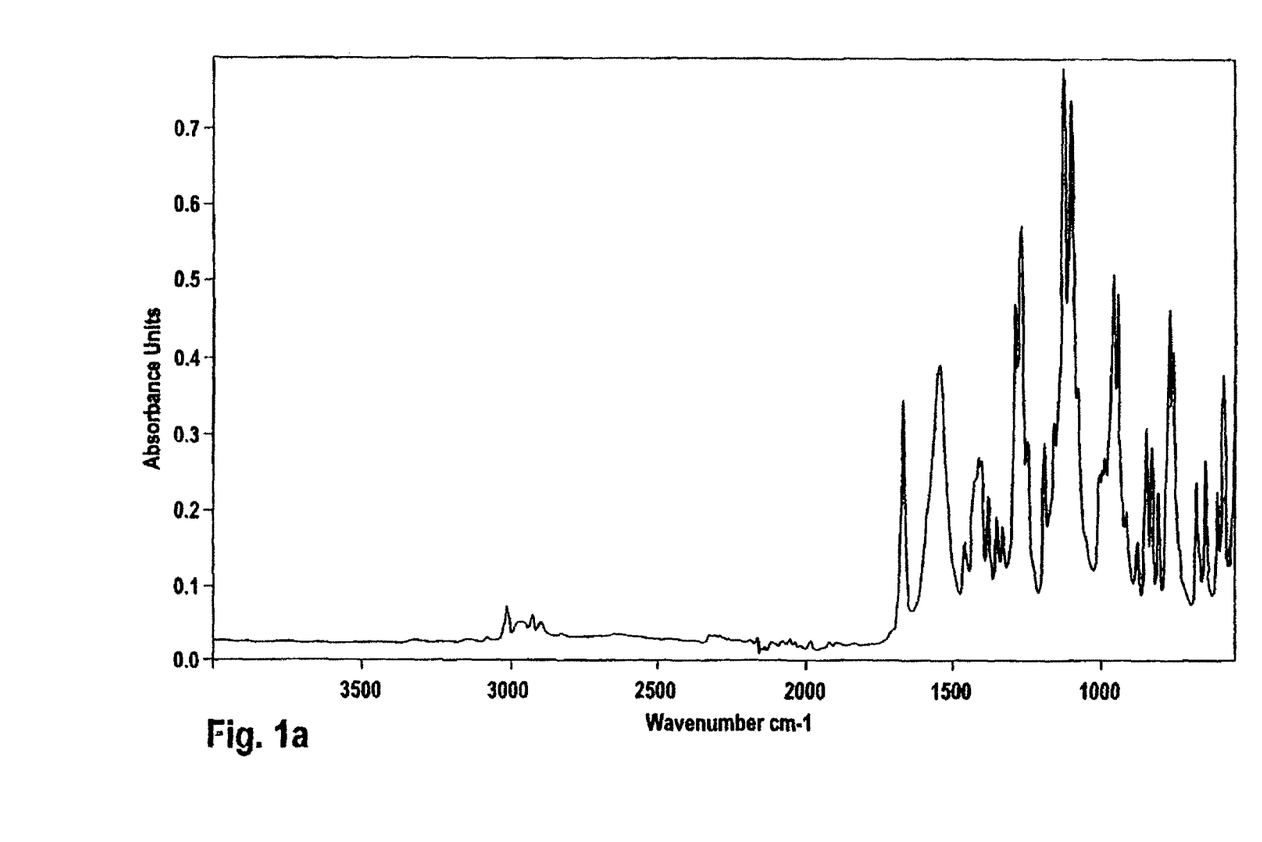
FIG. 1a shows the infrared spectrum of the crystal modification I of tembotrione. The values of the band maxima in wave numbers are listed in table 2.

The stable modification has a melting point of 124.0° C., a characteristic Raman spectrum (FIG. 1) and a characteristic infrared spectrum (FIG. 1a). Hereinbelow, it is referred to as crystal modification I.

Figure 2:
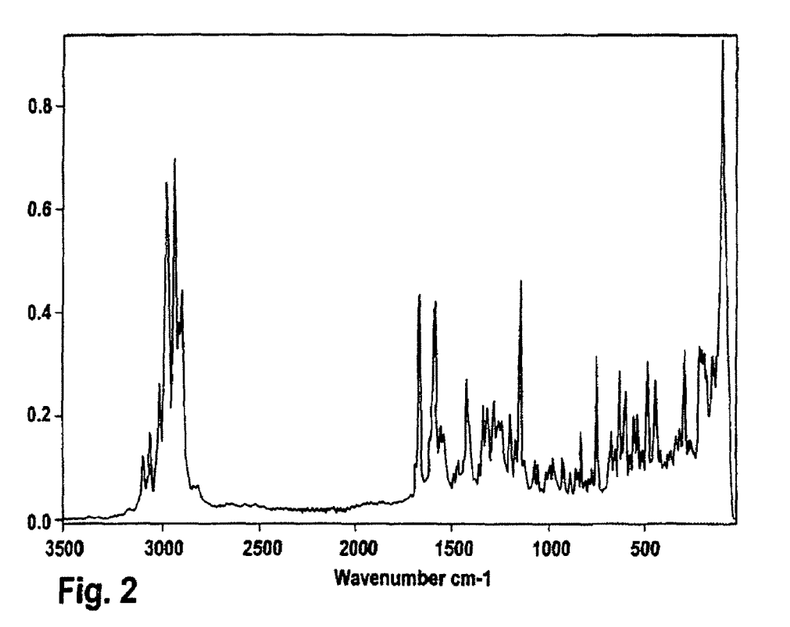
FIG. 2 shows the Raman spectrum of the crystal modification II of tembotrione. The values of the band maxima in wave numbers are listed in table 1.
Figure 2A:
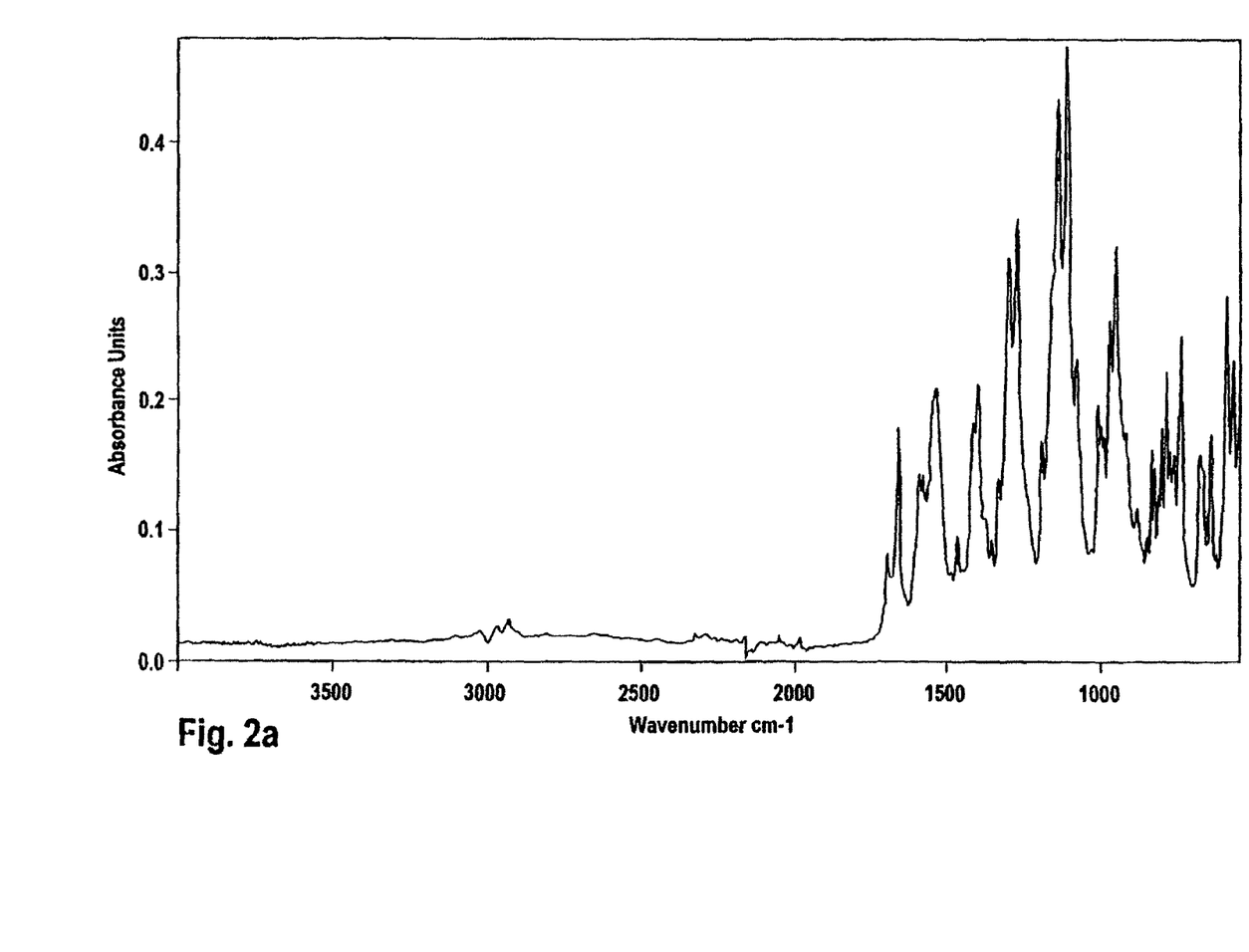
FIG. 2a shows the infrared spectrum of the crystal modification II of tembotrione. The values of the band maxima in wave numbers are listed in table 2.

The first metastable modification has a melting point of 123.9° C., a characteristic Raman spectrum (FIG. 2) and a characteristic infrared spectrum (FIG. 2a). Hereinbelow, it is referred to as crystal modification II.

Figure 3:
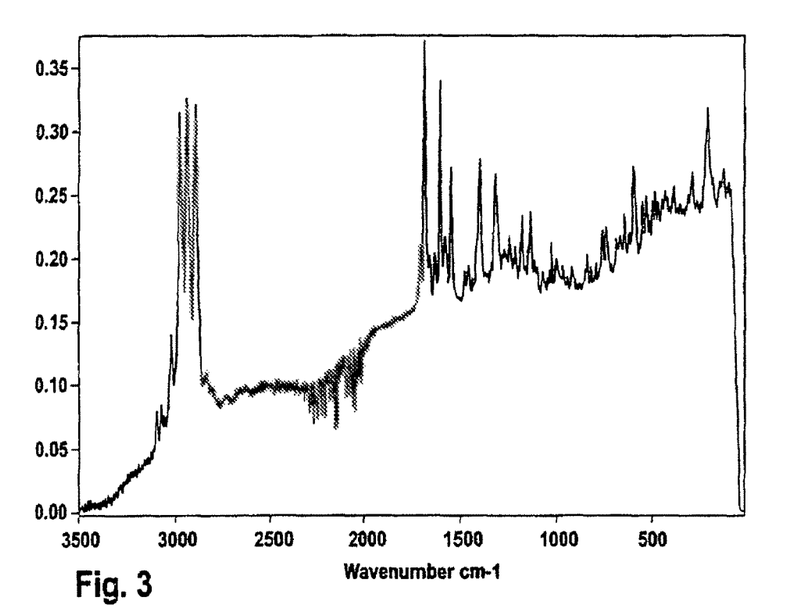
FIG. 3 shows the Raman spectrum of the crystal modification III of tembotrione. The values of the band maxima in wave numbers are listed in table 1.
Figure 3A:
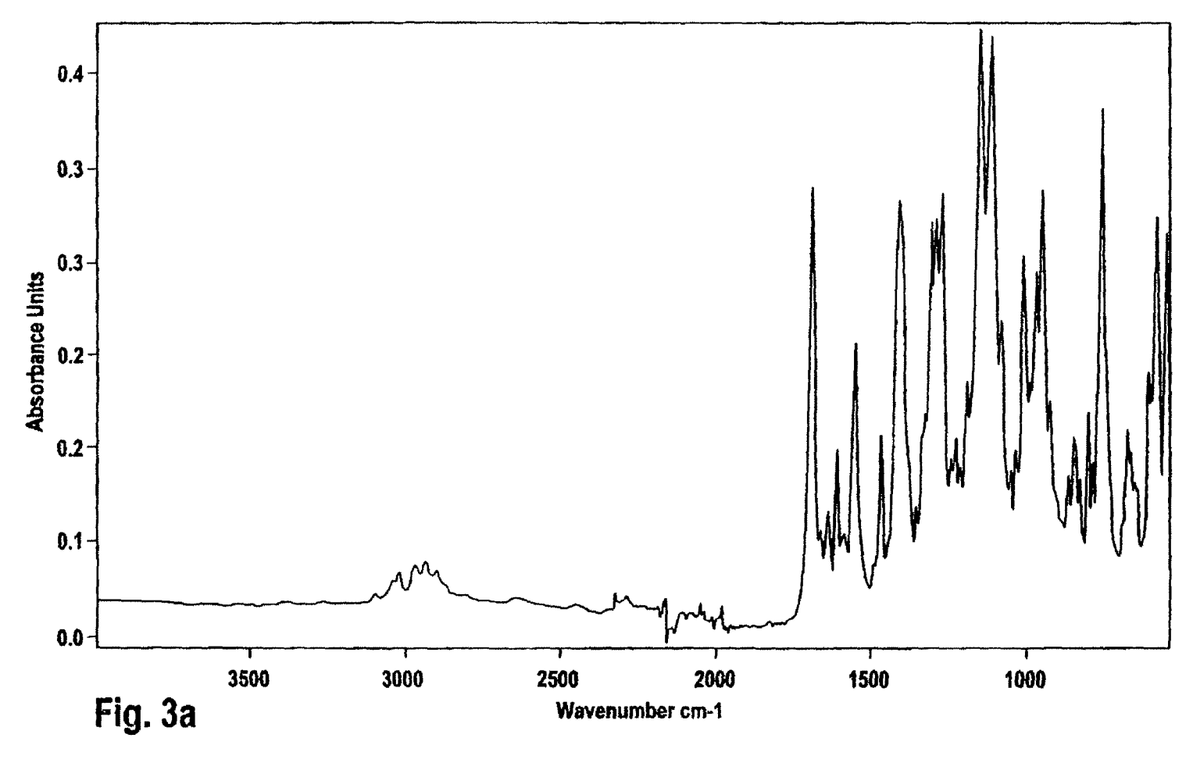
FIG. 3a shows the infrared spectrum of the crystal modification III of tembotrione. The values of the band maxima in wave numbers are listed in table 2.

The second metastable modification has a melting point of 121.6° C., a characteristic Raman spectrum (FIG. 3) and a characteristic infrared spectrum (FIG. 3a). Hereinbelow, it is referred to as crystal modification III.

The single-crystal structural analysis of the crystal modification I of tembotrione shows the characteristic bond angles and bond lengths for this crystal modification, which are stated in table 3.

The single-crystal structural analysis of the crystal modification II of tembotrione shows the characteristic bond angles and bond lengths for this crystal modification, which are stated in table 4.

The x-ray powder diffractometry of the crystal modification I of tembotrione shows peaks characteristic for this crystal modification, which are stated in table 5.

The x-ray powder diffractometry of the crystal modification II of tembotrione shows peaks characteristic for this crystal modification, which are stated in table 6.

Further crystallographic data of the crystal modifications I and II of tembotrione are stated in table 7.

TABLE 1

Band maxima of the Raman spectra in [cm⁻¹]

| Crystal modification I | | Crystal modification II | | Crystal modification III | |
|---|---|---|---|---|---|
| 91 | 921 | 94 | 976 | 85 | 867 |
| 130 | 952 | 146 | 992 | 92 | 891 |
| 171 | 968 | 181 | 1015 | 95 | 899 |
| 192 | 1002 | 203 | 1055 | 108 | 927 |
| 213 | 1053 | 215 | 1072 | 124 | 957 |
| 265 | 1075 | 253 | 1123 | 145 | 977 |
| 279 | 1116 | 292 | 1144 | 215 | 1004 |
| 291 | 1141 | 313 | 1171 | 269 | 1008 |
| 311 | 1166 | 334 | 1196 | 299 | 1037 |
| 363 | 1176 | 360 | 1239 | 315 | 1050 |
| 402 | 1197 | 378 | 1255 | 361 | 1081 |
| 431 | 1272 | 393 | 1281 | 371 | 1112 |
| 445 | 1289 | 416 | 1315 | 392 | 1129 |
| 460 | 1300 | 441 | 1335 | 434 | 1144 |
| 490 | 1325 | 481 | 1356 | 440 | 1154 |
| 507 | 1337 | 508 | 1420 | 449 | 1188 |
| 517 | 1358 | 535 | 1435 | 456 | 1226 |
| 540 | 1377 | 550 | 1466 | 474 | 1238 |
| 550 | 1418 | 571 | 1487 | 480 | 1254 |
| 599 | 1461 | 594 | 1538 | 493 | 1279 |
| 613 | 1557 | 626 | 1554 | 506 | 1286 |
| 655 | 1587 | 649 | 1584 | 513 | 1326 |
| 675 | 1665 | 672 | 1610 | 522 | 1353 |
| 687 | 1679 | 746 | 1662 | 539 | 1410 |
| 738 | 2888 | 782 | 1681 | 550 | 1445 |
| 775 | 2925 | 791 | 2895 | 557 | 1453 |
| 813 | 2971 | 807 | 2908 | 575 | 1469 |
| 836 | 2978 | 830 | 2928 | 579 | 1487 |
| 853 | 3010 | 845 | 2971 | 591 | 1553 |
| 883 | 3075 | 855 | 3011 | 604 | 1583 |
| | | 885 | 3062 | 625 | 1610 |
| | | 919 | 3096 | 653 | 1637 |
| | | 927 | | 670 | 1663 |
| | | | | 684 | 1684 |
| | | | | 694 | 1711 |
| | | | | 707 | 2838 |
| | | | | 722 | 2892 |
| | | | | 750 | 2937 |
| | | | | 768 | 2973 |
| | | | | 805 | 3020 |
| | | | | 832 | 3073 |
| | | | | 850 | 3099 |

TABLE 2

Band maxima of the infrared spectra in [cm⁻¹]

| Crystal modification I | | Crystal modification II | | Crystal modification III | |
|---|---|---|---|---|---|
| 593 | 1164 | 555 | 1033 | 555 | 1154 |
| 612 | 1196 | 571 | 1082 | 585 | 1190 |
| 654 | 1253 | 592 | 1116 | 604 | 1211 |
| 686 | 1282 | 625 | 1142 | 611 | 1226 |
| 765 | 1298 | 645 | 1194 | 666 | 1238 |
| 777 | 1336 | 680 | 1275 | 678 | 1273 |
| 786 | 1356 | 743 | 1299 | 766 | 1293 |
| 813 | 1386 | 766 | 1333 | 778 | 1309 |
| 836 | 1409 | 777 | 1353 | 791 | 1325 |
| 853 | 1417 | 789 | 1375 | 804 | 1350 |
| 883 | 1461 | 804 | 1400 | 831 | 1414 |
| 921 | 1553 | 816 | 1413 | 851 | 1467 |
| 951 | 1675 | 828 | 1464 | 867 | 1553 |
| 966 | 2897 | 838 | 1538 | 927 | 1584 |
| 994 | 2926 | 853 | 1580 | 955 | 1611 |
| 1010 | 2959 | 883 | 1591 | 971 | 1641 |
| 1085 | 3010 | 918 | 1660 | 988 | 1662 |
| 1112 | 3075 | 927 | 1695 | 1016 | 1696 |
| 1138 | | 956 | 2929 | 1034 | 2901 |
| | | 973 | 2968 | 1052 | 2938 |
| | | 991 | 3023 | 1081 | 2972 |
| | | 1001 | 3098 | 1119 | 3023 |
| | | 1012 | | 1144 | 3099 |

TABLE 3

Bond lengths [Å] and bond angles [°] of the crystal modification I

| Bond | Å (°) | Bond | Å (°) |
|---|---|---|---|
| CL(1)—C(3) | 1.732(2) | O(6)—C(17) | 1.305(3) |
| S(1)—O(2) | 1.4377(17) | C(9)—C(10) | 1.486(3) |
| S(1)—O(1) | 1.439(2) | C(11)—C(12) | 1.441(3) |
| S(1)—C(7) | 1.755(3) | C(12)—C(17) | 1.395(3) |
| S(1)—C(1) | 1.784(2) | C(12)—C(13) | 1.472(3) |
| C(1)—C(6) | 1.391(3) | C(13)—C(14) | 1.516(3) |
| C(1)—C(2) | 1.405(3) | C(14)—C(15) | 1.505(4) |
| F(1)—C(10) | 1.328(3) | C(15)—C(16) | 1.515(4) |
| C(2)—C(3) | 1.400(3) | C(16)—C(17) | 1.491(3) |
| C(2)—C(8) | 1.511(3) | O(3)—C(9)—C(10) | 107.7(2) |
| F(2)—C(10) | 1.316(3) | F(2)—C(10)—F(1) | 105.9(3) |
| C(3)—C(4) | 1.390(3) | F(2)—C(10)—F(3) | 106.8(2) |
| O(3)—C(9) | 1.407(4) | F(1)—C(10)—F(3) | 106.6(2) |
| O(3)—C(8) | 1.427(3) | F(2)—C(10)—C(9) | 114.6(2) |
| F(3)—C(10) | 1.331(4) | F(1)—C(10)—C(9) | 111.3(2) |
| O(4)—C(11) | 1.245(3) | F(3)—C(10)—C(9) | 111.2(3) |
| C(4)—C(5) | 1.387(3) | O(4)—C(11)—C(12) | 121.6(2) |
| C(4)—C(11) | 1.502(3) | O(4)—C(11)—C(4) | 115.24(19) |
| O(5)—C(13) | 1.219(3) | C(12)—C(11)—C(4) | 123.02(19) |
| C(5)—C(6) | 1.387(3) | C(17)—C(12)—C(11) | 117.8(2) |
| O(2)—S(1)—O(1) | 117.41(13) | C(17)—C(12)—C(13) | 119.7(2) |
| O(2)—S(1)—C(7) | 109.36(14) | C(11)—C(12)—C(13) | 122.49(19) |
| O(1)—S(1)—C(7) | 108.37(12) | O(5)—C(13)—C(12) | 122.2(2) |
| O(2)—S(1)—C(1) | 109.85(10) | O(5)—C(13)—C(14) | 120.4(2) |
| O(1)—S(1)—C(1) | 107.25(11) | C(12)—C(13)—C(14) | 117.2(2) |
| C(7)—S(1)—C(1) | 103.72(12) | C(15)—C(14)—C(13) | 114.9(2) |
| C(6)—C(1)—C(2) | 121.89(19) | C(14)—C(15)—C(16) | 110.0(2) |
| C(6)—C(1)—S(1) | 114.88(16) | C(17)—C(16)—C(15) | 111.2(2) |
| C(2)—C(1)—S(1) | 123.15(16) | O(6)—C(17)—C(12) | 122.0(2) |
| C(3)—C(2)—C(1) | 116.25(19) | O(6)—C(17)—C(16) | 115.4(2) |
| C(3)—C(2)—C(8) | 118.4(2) | C(12)—C(17)—C(16) | 122.6(2) |
| C(1)—C(2)—C(8) | 125.3(2) | | |
| C(4)—C(3)—C(2) | 122.7(2) | | |
| C(4)—C(3)—Cl(1) | 116.81(16) | | |
| C(2)—C(3)—Cl(1) | 120.43(17) | | |
| C(9)—O(3)—C(8) | 112.98(19) | | |
| C(5)—C(4)—C(3) | 119.1(2) | | |
| C(5)—C(4)—C(11) | 119.83(19) | | |
| C(3)—C(4)—C(11) | 120.7(2) | | |
| C(6)—C(5)—C(4) | 120.1(2) | | |
| C(5)—C(6)—C(1) | 119.8(2) | | |
| O(3)—C(8)—C(2) | 111.96(18) | | |

TABLE 4

Bond length [Å] and bond angles of the crystal modification II

| Bond | Å (°) | Bond | Å (°) |
|---|---|---|---|
| Cl(1)—C(3) | 1.7352(16) | C(9B)—C(10B) | 1.505(5) |
| S(1)—O(1) | 1.4294(14) | C(10B)—F(3B) | 1.323(5) |
| S(1)—O(2) | 1.4297(16) | C(10B)—F(1B) | 1.328(5) |
| S(1)—C(7) | 1.743(3) | C(10B)—F(2B) | 1.361(11) |
| S(1)—C(1) | 1.7843(16) | C(11)—C(12) | 1.444(2) |
| C(1)—C(6) | 1.381(2) | C(12)—C(13) | 1.390(2) |
| C(1)—C(2) | 1.407(2) | C(12)—C(17) | 1.469(2) |
| C(2)—C(3) | 1.391(2) | C(13)—C(14) | 1.480(2) |
| C(2)—C(8) | 1.506(2) | C(14)—C(15) | 1.510(3) |
| C(3)—C(4) | 1.392(2) | C(15)—C(16) | 1.506(3) |
| O(4)—C(11) | 1.243(2) | C(16)—C(17) | 1.512(2) |
| C(4)—C(5) | 1.384(2) | F(2A)—C(10A)—F(1A) | 106.2(6) |
| C(4)—C(11) | 1.505(2) | F(3A)—C(10A)—C(9A) | 114.0(9) |
| O(5)—C(13) | 1.312(2) | F(2A)—C(10A)—C(9A) | 112.2(5) |
| C(5)—C(6) | 1.380(2) | F(1A)—C(10A)—C(9A) | 113.8(5) |
| O(6)—C(17) | 1.220(2) | C(9B)—O(3B)—C(8) | 113.6(2) |
| C(8)—O(3A) | 1.381(4) | O(3B)—C(9B)—C(10B) | 112.3(3) |
| C(8)—O(3B) | 1.495(3) | F(3B)—C(10B)—F(1B) | 106.5(4) |
| O(3A)—C(9A) | 1.396(5) | F(3B)—C(10B)—F(2B) | 102.9(6) |
| C(9A)—C(10A) | 1.491(8) | F(1B)—C(10B)—F(2B) | 109.5(7) |
| C(10A)—F(3A) | 1.267(16) | F(3B)—C(10B)—C(9B) | 112.5(3) |
| C(10A)—F(2A) | 1.330(8) | F(1B)—C(10B)—C(9B) | 112.3(3) |
| C(10A)—F(1A) | 1.340(7) | F(2B)—C(10B)—C(9B) | 112.7(5) |
| O(3B)—C(9B) | 1.406(4) | O(4)—C(11)—C(12) | 122.17(15) |
| O(1)—S(1)—O(2) | 117.29(10) | O(4)—C(11)—C(4) | 116.88(14) |
| O(1)—S(1)—C(7) | 109.74(15) | C(12)—C(11)—C(4) | 120.93(14) |
| O(2)—S(1)—C(7) | 107.43(18) | C(13)—C(12)—C(11) | 118.64(14) |
| O(1)—S(1)—C(1) | 111.12(8) | C(13)—C(12)—C(17) | 119.17(14) |
| O(2)—S(1)—C(1) | 107.13(8) | C(11)—C(12)—C(17) | 122.10(14) |
| C(7)—S(1)—C(1) | 103.11(11) | O(5)—C(13)—C(12) | 122.28(15) |
| C(6)—C(1)—C(2) | 121.53(15) | O(5)—C(13)—C(14) | 114.49(15) |
| C(6)—C(1)—S(1) | 115.28(13) | C(12)—C(13)—C(14) | 123.23(15) |
| C(2)—C(1)—S(1) | 123.08(12) | C(13)—C(14)—C(15) | 111.94(15) |
| C(3)—C(2)—C(1) | 116.11(14) | C(16)—C(15)—C(14) | 110.06(16) |
| C(3)—C(2)—C(8) | 120.47(14) | C(15)—C(16)—C(17) | 113.94(15) |
| C(1)—C(2)—C(8) | 123.42(14) | O(6)—C(17)—C(12) | 122.32(14) |
| C(2)—C(3)—C(4) | 122.82(15) | O(6)—C(17)—C(16) | 119.85(15) |
| C(2)—C(3)—Cl(1) | 120.15(12) | C(12)—C(17)—C(16) | 117.72(14) |
| C(4)—C(3)—Cl(1) | 117.03(12) | | |
| C(5)—C(4)—C(3) | 119.20(15) | | |
| C(5)—C(4)—C(11) | 119.03(14) | | |
| C(3)—C(4)—C(11) | 121.76(14) | | |
| C(6)—C(5)—C(4) | 119.46(15) | | |
| C(5)—C(6)—C(1) | 120.70(16) | | |
| O(3A)—C(8)—O(3B) | 30.21(15) | | |
| O(3A)—C(8)—C(2) | 110.68(18) | | |
| O(3B)—C(8)—C(2) | 104.49(15) | | |
| C(8)—O(3A)—C(9A) | 116.4(3) | | |
| O(3A)—C(9A)—C(10A) | 112.2(4) | | |
| F(3A)—C(10A)—F(2A) | 110.4(11) | | |
| F(3A)—C(10A)—F(1A) | 99.2(10) | | |

TABLE 5

X-ray powder diffractometry pattern of the crystal modification I of tembotrione [2θ]

| | | | |
|---|---|---|---|
| 7.3765 | 20.8117 | 26.6207 | 32.4069 |
| 8.0674 | 21.1093 | 27.2879 | 32.8121 |
| 10.7988 | 21.5838 | 27.4979 | 33.1960 |
| 13.5030 | 21.6983 | 27.9884 | 33.5965 |
| 14.7553 | 23.5072 | 28.2728 | 34.4007 |
| 16.4462 | 23.9969 | 28.5989 | 35.1147 |
| 16.6192 | 24.3808 | 29.0017 | 35.7136 |
| 17.0512 | 24.8173 | 30.0318 | 35.9960 |
| 17.1467 | 25.0316 | 30.2456 | 36.4372 |
| 17.6444 | 25.2513 | 30.6058 | 36.7974 |
| 17.7792 | 25.5214 | 30.7628 | |
| 19.3008 | 25.7119 | 31.2971 | |
| 20.4034 | 25.9248 | 31.6675 | |

TABLE 6

X-ray powder diffractometry pattern of the crystal modification II of tembotrione [2θ]

| | | | |
|---|---|---|---|
| 7.3765 | 20.8117 | 26.6207 | 32.4069 |
| 8.0674 | 21.1093 | 27.2879 | 32.8121 |
| 10.7988 | 21.5838 | 27.4979 | 33.1960 |
| 13.5030 | 21.6983 | 27.9884 | 33.5965 |
| 14.7553 | 23.5072 | 28.2728 | 34.4007 |
| 16.4462 | 23.9969 | 28.5989 | 35.1147 |
| 16.6192 | 24.3808 | 29.0017 | 35.7136 |
| 17.0512 | 24.8173 | 30.0318 | 35.9960 |
| 17.1467 | 25.0316 | 30.2456 | 36.4372 |
| 17.6444 | 25.2513 | 30.6058 | 36.7974 |
| 17.7792 | 25.5214 | 30.7628 | |
| 19.3008 | 25.7119 | 31.2971 | |
| 20.4034 | 25.9248 | 31.6675 | |

TABLE 7

Crystallographic data

|  | Crystal modification I | | Crystal modification II | |
|---|---|---|---|---|
| Symmetry type | orthorhombic | | monocline | |
| Space group | Pna2$_1$ | | P2(1)/n | |
| Dimensions of the unit cell | a = 31.1647(18) Å | $\alpha$ = 90° | a = 15.8491(5) (18) Å | $\alpha$ = 90° |
|  | b = 10.3522(6) Å | $\beta$ = 90° | b = 7.1164(2) Å | $\beta$ = 95.721° |
|  | c = 5.5449(3) Å | $\gamma$ = 90° | c = 16.1656(6) Å | $\gamma$ = 90° |
| Volume of the unit cell | 1788.91(18) Å3 | | 1814.21(10) Å3 | |
| Coordination number | 4 | | 4 | |
| Density (calculated) | 1.637 Mg/m$^3$ | | 1.614 Mg/m$^3$ | |

DESCRIPTION OF THE INVENTION

The melting points were determined by means of DSC (Pyris 1 from Perkin Elmer, heating rate 10 K min$^{-1}$). For determining the Raman spectra, at least two spectra with 128 scans each were recorded for each batch by means of an RFS 100/S FT Raman from Bruker. The infrared spectra were recorded using an FT-IR spectrometer (from Bruker, Tensor 37), with in each case 64 scans.

The solid density was determined by the SOP 5024 density determination method using an Ultrapyknometer 1000 T from Quanta-Chrome or determined from the single-crystal x-ray structure analysis (SCS). The single-crystal x-ray structure analysis (SCS) was carried out using an M18X-HF rotating anode with MoK$\alpha$ radiation from MACScience Co and a SMART-CCD-1000 detector from Bruker-AXS. The data were processed using the programs SAINT-NT V 5.0 (data reduction, Bruker-AXS) and SADABS (absorption correction, Bruker-AXS). The resolution of the structure and the refinement were carried out using SHELXTL NT Version V5.1.

Preparation

Tembotrione can be prepared, for example, by the process mentioned in WO 00/21924. Depending on the nature of the solvent used in the final purification step and the temperatures used, tembotrione usually crystallizes as a mixture or in the form of one of the pure metastable crystal modifications II and III described here.

In a general manner, the thermodynamically stable crystal modification I of tembotrione can be prepared by suspending and/or dissolving the crystal modifications II and III of tembotrione obtainable according to WO 00/21924 or mixtures thereof in a suitable solvent and treating it at temperatures of from 0° C. to 80° C. until it is converted quantitatively into the thermodynamically stable crystal modification I.

Accordingly, the invention furthermore provides a process for preparing the thermodynamically stable crystal modification I of tembotrione wherein the crystal modifications II and III of tembotrione or mixtures thereof are suspended and/or dissolved in solvents and treated at temperatures of from 0° C. to 80° C. up to the quantitative conversion into the thermodynamically stable crystal modification I.

Suitable solvents which may be employed in this process are, for example, lower alcohols, such as methanol, ethanol, 2-propanol, or ketones, such as acetone, 2-butanone, which may also be used as a mixture with water. Here, lower alcohols or ketones refer to compounds having one to ten carbon atoms, preferably one to five carbon atoms. Further suitable solvents are benzene, toluene and chlorobenzene.

The conversion into the thermodynamically stable crystal modification I takes place at temperatures of below 100° C., preferably at temperatures of from 0° C. to 80° C., particularly preferably at temperatures of from 60° C. to 80° C., very particularly preferably at temperatures of from 50° C. to 80° C. The duration of the conversion depends on the temperature and the type of solvent. The duration of the conversion furthermore depends on whether seed crystals of the crystal modification I are used. In general, the conversion into the crystal modification I can be achieved directly, without the use of seed crystals, when the crystals of crystal modifications II and III or mixtures thereof are dissolved completely at elevated temperature when the solution is cooled to crystal at room temperature. Cooling to room temperature is preferably carried out using a cooling rate of less than 25° C., particularly preferably a cooling rate of less than 20° C. The conversion of a suspension of crystal modifications II and III or mixtures thereof can generally be effected without the use of seed crystals over a period of 14 days. If seed crystals of the crystal modification I are used in the conversion of a suspension, a duration of treatment of from 24 to 48 hours is generally sufficient for achieving a quantitative conversion of the crystals into the crystal modification I.

The resulting crystals of the crystal modification I are finally separated off and dried at room temperature or elevated temperature to constant weight in order to remove the solvent.

The stable crystal modification I can also be obtained by grinding under high pressure from the crystal modifications II and III or mixtures thereof. A suitable pressure is a pressure of at least 5 bar.

By virtue of its stability, the crystal modification I is outstandingly suitable for preparing formulations, in particular suspension formulations, of crop protection agents. Accordingly, the invention also provides for crop protection compositions comprising the crystal modification I of tembotrione on its own or as a mixture with auxiliaries and carriers, and also as a mixture with other active compounds. The invention also includes mixtures of the crystal modification I of tembotrione with the crystal modifications II and III of tembotrione, for example those which occur at any point in the process according to the invention for the conversion of the crystal modifications II and III or mixtures thereof into the crystal modification I. Preference is given to an active compound quality comprising more than 20% by weight of the crystal modification I of tembotrione, particularly preferably comprising more than 90% by weight, very particularly preferably comprising more than 95% by weight and most preferably comprising more than 98% by weight.

If appropriate tembotrione in the crystal modification I is mixed with one or more other herbicides. Such mixtures also benefit from the advantageous properties of the crystal modification I according to the invention.

By virtue of its stability, the crystal modification I of tembotrione is in general suitable as starting material for the preparation of any tembotrione-comprising crop protection formulations, even if, after formulation, the tembotrione is no longer present in this form but, for example, in dissolved form.

Accordingly, the invention also provides processes for preparing tembotrione-comprising crop protection formulations which use the crystal modification I of tembotrione, and also to tembotrione-comprising crop protection formulations obtained from the crystal modification I of tembotrione. By using the crystal modification I, the safety is increased for preparations of tembotrione and the risk of incorrect dosages is thus reduced.

The crystal modification I of tembotrione can be converted in a known manner into the customary formulations, such as suspension concentrates, colloidal concentrates, dispersible concentrates, emulsifiable concentrates (emulsion concentrates), emulsion dressings, suspension dressings, granules, microgranules, suspoemulsiones, oil dispersions, water-soluble granules, water-soluble concentrates and water-dispersible granules, using suitable auxiliaries and carriers or solvents. Here, the active compound should be present in a concentration of from 0.5 to 90% by weight of the total mixture, i.e. in amounts which are sufficient to achieve the necessary dosage level. The formulations are prepared, for example, by extending the crystal modification I of tembotrione with solvents and/or carriers, if appropriate if the use of emulsifiers and/or dispersants, and/or other auxiliaries, such as, for example, penetrants.

Application is effected in the customary manner by bringing the unwanted plants and/or their habitat into contact with the active compound or its formulation.

Tembotrione in the crystal modification I has an outstanding herbicidal action against representatives of the group consisting both of the monocotyledonous and the dicotyledonous plants. Accordingly, the invention also provides the use of the crystal modification I of tembotrione for preparing a crop protection composition for treating weed infestation.

Dicotyledonous plants of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datum, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Monocotyledonous plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

By virtue of its good compatibility with crop plants, the crystal modification I according to the invention of tembotrione is suitable for controlling unwanted plants in crops of, for example, wheat, barley, oats, rye, rice, corn, sugar beet, sugar cane, cotton and soya beans, in particular in rice, corn and sugar cane.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the crystal modification I according to the invention of tembotrione is carried out directly or by allowing the compounds to act on their surroundings, environment or storage space by the customary treatment methods, for example by immersion, spraying, evaporation, fogging, scattering, painting on.

The crystal modification I according to the invention of tembotrione can, as already discussed above, be converted into the customary formulations such as solutions, emulsions, wettable powders, suspensions, powders, dusts, pastes, soluble powders, granules, suspoemulsion concentrates, natural and synthetic materials impregnated with active compound, and microencapsulations in polymeric materials.

These formulations are produced in a known manner, for example by mixing the active compounds with extenders, that is liquid solvents and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, corn cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates; suitable dispersants are: for example lignosulfite waste liquors and methylcellulose.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound in the crystal modification I according to the invention, preferably between 0.5 and 90%.

For controlling weeds, the crystal modification I according to the invention of tembotrione, as such or in their formulations, can also be used as mixtures with other agrochemically active compounds, for example known herbicides and/or substances which improve the compatibility with crop plants ("safeners"), finished formulations or tank mixes being possible. Also possible are thus mixtures with weedkillers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPIC, esprocarb, ethalfluralin, ethametsulfuron (-methyl), ethofumesate, ethoxyfen, ethoxysulfuron, etobenzanid, fenoxaprop (—P-ethyl), fentrazamide, flamprop (-isopropyl, -isopropyl-L, -methyl), flazasulfuron, florasulam, fluazifop (—P-butyl), fluazolate, flucarbazone (-sodium), flufenacet, flufenpyr, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, —P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulfuron (-methyl, -sodium), mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrasulfotole, pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (—P-ethyl, —P-tefuryl), rimsulfuron, sethoxydim, simazine, simetryn, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore suitable for the mixtures are known safeners, for example AD-67, BAS-145138, benoxacor, cloquintocet (-mexyl), cyometrinil, cyprosulfamide, 2,4-D, DKA-24, dichlormid, dymron, fenclorim, fenchlorazol (-ethyl), flurazole, fluxofenim, furilazole, isoxadifen (-ethyl), MCPA, mecoprop (—P), mefenpyr (-diethyl), MG-191, oxabetrinil, PPG-1292, R-29148.

A mixture with other known active compounds, such as fungicides, insecticides, acaricides, nematicides, bird repellents, plant nutrients and soil improvers is also possible.

The crystal modification I according to the invention of tembotrione can be used as such, in the form of their formulations or in the use forms prepared therefrom by further dilution, such as ready-to-use solutions, suspensions, emulsions, powders, pastes and granules. The application is carried out in a customary manner, for example by watering, spraying, atomizing, broadcasting.

The crystal modification I according to the invention of tembotrione can be applied both before and after emergence of the plants. They can also be incorporated into the soil prior to sowing.

The application rate of active compound can vary within a relatively large range. It depends essentially on the nature of the desired effect. In general, the application rates are between 1 g and 1 kg of active compound per hectare of soil, preferably between 5 g and 500 g per ha.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above. Particularly preferably, plants of the plant cultivars which are in each case commercially available or in use are treated according to the invention. Plant cultivars are understood as meaning plants with specific properties ("traits") which have been obtained by conventional cultivation, by mutagenesis or else by recombinant DNA techniques. These may be cultivars, biotypes or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or widenings of the activity spectrum and/or an increase in the activity of the substances and compositions that can be used according to the invention also in combination with other agrochemical active compounds, better crop plant growth, increased tolerance of the crop plants to high or low temperatures, increased tolerance of the crop plants to drought or to water or soil salt content, increased flowering performance, easier harvesting, accelerated maturation, higher harvest yields, better quality and/or a higher nutritional value of the harvested products, better storage stability and/or processability of the harvested products which exceed the effects which were actually to be expected are possible.

The preferred transgenic plants or plant cultivars (i.e. those obtained by genetic engineering) which are to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), soya beans, potatoes, cotton, oilseed rape and also in particular corn and also fruit plants (with the fruits apples, pears, citrus fruits and grapes), and particular emphasis is given to corn, soya beans, potatoes, cotton and oilseed rape. Traits that are emphasized are in particular increased defense of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits which are also particularly emphasized are the increased resistance of plants to fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulfonylureas, glyphosate or phosphinothricin (for example the "PAT" gene). The genes which impart the desired traits in question can also be present in combination with one another in the transgenic plants. Examples of "Bt plants" which may be mentioned are corn varieties, cotton varieties, soya bean varieties and potato varieties which are sold under the trade names YIELD GARD® (for example corn, cotton, soya beans), KnockOut® (for example corn), StarLink® (for example corn), Bollgard® (cotton), Nucotn® (cotton) and NewLeaf® (potato). Examples of herbicide-tolerant plants which may be mentioned are corn varieties, cotton varieties and soya bean varieties which are sold under the trade names Roundup Ready® (tolerance to glyphosates, for example corn, cotton, soya bean), Liberty Link® (tolerance to phosphinothricin, for example oilseed rape), IMI® (tolerance to imidazolinones) and STS® (tolerance to sulfonylureas, for example corn). Herbicide-resistant plants (plants bred in a conventional manner for herbicide tolerance) which may be mentioned include the varieties sold under the name Clearfield® (for example corn). Of course, these statements also apply to plant cultivars having these genetic traits or genetic traits still to be developed, which cultivars will be developed and/or marketed in the future.

WORKING EXAMPLES

Preparation of the Thermodynamically Stable Crystal Modification I

At boiling point (56° C.) 2 g of tembotrione were dissolved completely in acetone and then slowly, i.e. at a cooling rate of less than 20° C./h, cooled to room temperature. The crystals are filtered off and dried at temperatures of <60° C.

Preparation of the Metastable Crystal Modification II

At boiling point (78° C.), 2 g of tembotrione were dissolved completely in ethanol. The clear solution was then slowly, i.e. at a cooling rate of less than 20° C./h, cooled to 7° C. The crystals are filtered off and dried at temperatures of <60° C.

Preparation of the Metastable Crystal Modification III

At boiling point (111° C.), 2 g of tembotrione were dissolved completely in toluene. The clear solution was then slowly, i.e. at a cooling rate of less than 20° C./h, cooled to 7° C. The crystals are filtered off and dried at temperatures of <60° C.

Stability Test

Compared to an oil dispersion of tembotrione of the crystal modification II, III or a mixture thereof, an oil dispersion of tembotrione of the crystal modification I shows no signs of agglomeration and precipitation even after several weeks of storage.

The invention claimed is:

1. A crystal modification of 2-({2-chloro-4-(methylsulfonyl)-3-[(2,2,2-trifluoro-ethoxy)methyl]phenyl}carbonyl)cyclohexan-1,3-dione (tembotrione) in an orthorhombic system, where the crystal modification has (a) an infrared spectrum having the following band maxima stated in $cm^{-1}$:

| | | | |
|---|---|---|---|
| 593 | 883 | 1196 | 1553 |
| 612 | 921 | 1253 | 1675 |
| 654 | 951 | 1282 | 2897 |
| 686 | 966 | 1298 | 2926 |
| 765 | 994 | 1336 | 2959 |
| 777 | 1010 | 1356 | 3010 |
| 786 | 1085 | 1386 | 3075 |
| 813 | 1112 | 1409 | |
| 836 | 1138 | 1417 | |
| 853 | 1164 | 1461 | | and/or (b) a Raman spectrum having the following band maxima stated in $cm^{-1}$:

| | | | |
|---|---|---|---|
| 91 | 507 | 921 | 1337 |
| 130 | 517 | 952 | 1358 |
| 171 | 540 | 968 | 1377 |
| 192 | 550 | 1002 | 1418 |
| 213 | 599 | 1053 | 1461 |
| 265 | 613 | 1075 | 1557 |
| 279 | 655 | 1116 | 1587 |

| | | | |
|---|---|---|---|
| 291 | 675 | 1141 | 1665 |
| 311 | 687 | 1166 | 1679 |
| 363 | 738 | 1176 | 2888 |
| 402 | 775 | 1197 | 2925 |
| 431 | 813 | 1272 | 2971 |
| 445 | 836 | 1289 | 2978 |
| 460 | 853 | 1300 | 3010 |
| 490 | 883 | 1325 | 3075 | and/or (c) an X-ray powder diffractometry pattern having the following peaks stated in degrees 2θ:

| | | | |
|---|---|---|---|
| 7.3765 | 20.8117 | 26.6207 | 32.4069 |
| 8.0674 | 21.1093 | 27.2879 | 32.8121 |
| 10.7988 | 21.5838 | 27.4979 | 33.1960 |
| 13.5030 | 21.6983 | 27.9884 | 33.5965 |
| 14.7553 | 23.5072 | 28.2728 | 34.4007 |
| 16.4462 | 23.9969 | 28.5989 | 35.1147 |
| 16.6192 | 24.3808 | 29.0017 | 35.7136 |
| 17.0512 | 24.8173 | 30.0318 | 35.9960 |
| 17.1467 | 25.0316 | 30.2456 | 36.4372 |
| 17.6444 | 25.2513 | 30.6058 | 36.7974. |
| 17.7792 | 25.5214 | 30.7628 | |
| 19.3008 | 25.7119 | 31.2971 | |
| 20.4034 | 25.9248 | 31.6675 | |

2. The crystal modification as claimed in claim 1, where the orthorhombic system has the space group Pna2$_1$.

3. The crystal modification as claimed in claim 1, wherein the unit cell has the following dimensions:

| | |
|---|---|
| a = 31.1647(18) Å | = 90° |
| b = 10.3522(6) Å | = 90° |
| c = 5.5449(3) Å | = 90°. |

4. The crystal modification as claimed in claim 1 having a melting point of 124.0° C.

5. A herbicidal composition characterized by a content of thermodynamically stable crystal modification of tembotrione as claimed in claim 1 and at least one extender and/or surface-active auxiliary.

6. A herbicidal composition comprising the thermodynamically stable crystal modification of tembotrione as claimed in claim 1 and a metastable crystal modification or a mixture of the metastable crystal modification of tembotrione, wherein the composition comprises at least 80% by weight of the stable crystal modification.

7. A composition for controlling unwanted plants comprising the thermodynamically stable crystal modification of tembotrione as claimed in claim 1.

8. A method for controlling unwanted plants, comprising allowing the thermodynamically stable crystal modification of tembotrione as claimed in claim 1 to act on the unwanted plants and/or a habitat thereof.

9. The method as claimed in claim 8 for controlling harmful plants in crops of monocotyledonous plants.

10. The method as claimed in claim 8, where the crop plants are genetically modified and/or have been obtained by mutation selection.

11. The method of claim 9, where the crop plants are genetically modified and/or have been obtained by mutation selection.

* * * * *